(12) United States Patent
Goldvasser

(10) Patent No.: US 12,097,016 B2
(45) Date of Patent: Sep. 24, 2024

(54) BLOOD FLOW RATE MEASUREMENT SYSTEM

(71) Applicant: Abiomed, Inc., Danvers, MA (US)

(72) Inventor: Dov Goldvasser, Framingham, MA (US)

(73) Assignee: ABIOMED, INC., Danvers, MA (US)

( * ) Notice: Subject to any disclaimer, the term of this patent is extended or adjusted under 35 U.S.C. 154(b) by 1048 days.

(21) Appl. No.: 16/353,132

(22) Filed: Mar. 14, 2019

(65) Prior Publication Data
US 2020/0288988 A1  Sep. 17, 2020

(51) Int. Cl.
*A61B 5/027* (2006.01)
*A61B 5/00* (2006.01)
(Continued)

(52) U.S. Cl.
CPC .......... *A61B 5/027* (2013.01); *A61B 5/6852* (2013.01); *A61M 60/13* (2021.01);
(Continued)

(58) Field of Classification Search
None
See application file for complete search history.

(56) References Cited

U.S. PATENT DOCUMENTS 3,757,773 A * 9/1973 Kolin .................. A61B 5/1076
73/861.16
3,995,491 A * 12/1976 Wolfla, II .......... A63B 22/0605
74/551.8
(Continued)

FOREIGN PATENT DOCUMENTS

CN 1311700 A 9/2001
CN 2555499 Y 6/2003
(Continued)

OTHER PUBLICATIONS

Sarnoff, Stanley J., and Erik Berglund. "The Potter electroturbinometer: an instrument for recording total systemic blood flow in the dog." Circulation Research 1.4 (1953): 331-336. (Year: 1953).*
(Continued)

*Primary Examiner* — Puya Agahi
*Assistant Examiner* — Jairo H Portillo
(74) *Attorney, Agent, or Firm* — Botos Churchill IP Law LLP

(57) ABSTRACT

A blood flow rate measurement system measures fluid flow rate in a blood vessel having a catheter-based heart pump inserted therein, without relying on measurements of electric current drawn by a motor that drives the heart pump. A turbine is disposed at or near a distal end of the heart pump catheter. Blood or other fluid flowing through the blood vessel urges blades of the turbine to rotate. The turbine is mechanically coupled to a signal generator, which generates a signal indicative of a rotational speed of the turbine, which is dependent, at least in part, on speed of the fluid flowing through the blood vessel. A tachometer, external to the body of the patient, calculates the blood flow rate from the rotational speed of the turbine. In some cases, the blades are collapsible, to reduce diameter of the turbine, thereby facilitating insertion of the system into the blood vessel.

20 Claims, 8 Drawing Sheets

(51) Int. Cl.
   *A61M 60/13* (2021.01)
   *A61M 60/135* (2021.01)
   *A61M 60/216* (2021.01)
   *A61M 60/422* (2021.01)
   *G01F 1/075* (2006.01)
(52) U.S. Cl.
   CPC ........ *A61M 60/135* (2021.01); *A61M 60/216* (2021.01); *A61M 60/422* (2021.01); *G01F 1/075* (2013.01)

(56) References Cited

U.S. PATENT DOCUMENTS

| | | | |
|---|---|---|---|
| 5,709,670 A * | 1/1998 | Vancaillie | A61B 5/02042 604/246 |
| 6,368,075 B1 | 4/2002 | Fremerey | |
| 8,382,423 B1 * | 2/2013 | Frodis | A61B 17/3201 415/904 |
| 8,814,933 B2 | 8/2014 | Siess | |
| 8,932,141 B2 | 1/2015 | Liebing | |
| 8,944,748 B2 | 2/2015 | Liebing | |
| 9,067,006 B2 | 6/2015 | Toellner | |
| 9,314,558 B2 | 4/2016 | Er | |
| 9,339,596 B2 | 5/2016 | Roehn | |
| 9,416,783 B2 | 8/2016 | Schumacher et al. | |
| 9,416,791 B2 | 8/2016 | Toellner | |
| 9,611,743 B2 | 4/2017 | Toellner et al. | |
| 9,642,984 B2 | 5/2017 | Schumacher et al. | |
| 9,750,860 B2 | 9/2017 | Schumacher | |
| 9,861,299 B1 * | 1/2018 | Jones | G16H 50/30 |
| 2002/0088285 A1 * | 7/2002 | Carrick | G01P 1/07 73/866.3 |
| 2003/0100911 A1 | 5/2003 | Nash et al. | |
| 2007/0119246 A1 | 5/2007 | Miyakoshi et al. | |
| 2008/0054745 A1 | 3/2008 | Sentmanat | |
| 2008/0103591 A1 | 5/2008 | Siess | |
| 2008/0319330 A1 * | 12/2008 | Juntunen | A61B 5/02438 455/66.1 |
| 2009/0093796 A1 | 4/2009 | Pfeffer et al. | |
| 2009/0134623 A1 * | 5/2009 | Krouse | F03B 13/08 415/4.1 |
| 2009/0138080 A1 | 5/2009 | Siess et al. | |
| 2010/0185216 A1 * | 7/2010 | Garrison | A61M 25/0662 606/144 |
| 2011/0004198 A1 * | 1/2011 | Hoch | A61B 5/412 604/523 |
| 2014/0039465 A1 | 2/2014 | Schulz et al. | |
| 2014/0303596 A1 | 10/2014 | Schumacher et al. | |
| 2015/0099989 A1 * | 4/2015 | Kobayashi | A61B 8/06 606/49 |
| 2015/0313453 A1 * | 11/2015 | Zelenka | A61B 8/445 600/463 |
| 2016/0000983 A1 * | 1/2016 | Mohl | A61M 60/88 600/16 |
| 2018/0080326 A1 | 3/2018 | Schumacher et al. | |
| 2018/0256797 A1 * | 9/2018 | Schenck | A61M 60/414 |
| 2018/0296742 A1 | 10/2018 | Toellner | |
| 2019/0269840 A1 * | 9/2019 | Tuval | A61M 60/13 |

FOREIGN PATENT DOCUMENTS

| | | |
|---|---|---|
| CN | 101448535 A | 6/2009 |
| JP | S60150420 U | 10/1985 |
| JP | 2003121215 A | 4/2003 |
| JP | 2003525561 A | 8/2003 |
| JP | 2008519624 A | 6/2008 |
| JP | 2010503369 A | 1/2010 |
| KR | 20140059789 A | 5/2014 |
| KR | 20150080482 A | 7/2015 |
| WO | 0006217 A1 | 2/2000 |
| WO | 2006051023 A1 | 5/2006 |
| WO | 2008027597 A2 | 3/2008 |
| WO | 2013025826 A1 | 2/2013 |
| WO | 2013028787 A1 | 2/2013 |
| WO | 2017021146 A1 | 2/2017 |
| WO | 2018067410 A1 | 4/2018 |
| WO | 2018073150 A1 | 4/2018 |
| WO | 2018096531 A1 | 5/2018 |
| WO | 2018193079 A1 | 10/2018 |

OTHER PUBLICATIONS

International Searching Authority—International Search Report—International Application No. PCT/US2019/062764 dated Feb. 17, 2020, together with the Written Opinion of the International Searching Authority, 13 pages.

Office Action issued in corresponding Chinese Patent Application No. 2019800938484 dated Jul. 8, 2022 (8 pp.).

Extended European Search Report issued in corresponding European Patent Application No. 23166270.1 dated Jun. 28, 2023 (5 pp.).

Office Action from corresponding Indian Patent Application No. 202117044099 dated Nov. 16, 2023 (6 pp.).

* cited by examiner

BLOOD FLOW RATE MEASUREMENT SYSTEM

TECHNICAL FIELD

The present invention relates to blood flow measurement systems and, more particularly, to catheter-mounted, turbine-driven blood flow measurement systems.

BACKGROUND

Many patients with coronary artery disease (CAD) would benefit from stent percutaneous coronary intervention (CPI) or coronary artery bypass graft surgery. However, some of these patients are considered to be too high-risk for complications that may occur during these procedures. Risk factors include: advanced age; history of disease, such as kidney disease, stroke or diabetes; location of the CAD, including left main or bifurcated disease; challenging plaque types, including calcified or long lesions; chronic total occlusion of the coronary arteries; previous open-heart surgery; and advanced heart failure.

Interventional cardiologists treat some of these high-risk patients with an advanced catheter-based procedure, referred to as complete or complex higher risk indicated percutaneous coronary intervention (CHIP). However, high-risk CAD patients that have also been diagnosed with advanced heart failure or severe heart valve disease are particularly vulnerable during CHIP procedures, due to weakened heart muscle, which compromises blood pressure and cannot pump blood efficiently to the body.

For a high-risk CAD patient, a ventricular assist device may be used during CHIP to provide temporary support to the patient's heart by assisting in blood circulation through the patient's cardiovascular system. For example, a catheter with a heart pump at one end may be inserted via a standard catheterization procedure through a femoral artery, into the ascending aorta, across the aortic valve and into the left ventricle. Once in place, the heart pump supports blood movement from the left ventricle, through inlet ports near the tip and the cannula to outlet ports and into the ascending aorta.

Temporarily, such as for less than about six hours, supporting the heart with a ventricular assist device during CHIP is referred to as protected PCI. Exemplary ventricular assist devices include Impella 2.5® and Impella CP® heart pumps available from Abiomed, Inc., Danvers, MA. Although the Impella 2.5 heart pump has a catheter diameter of only 9 Fr, and a pump motor diameter of only 12 Fr (14 Fr for the Impella CP heart pump), smaller diameter catheters and motor diameters are highly desirable.

BRIEF SUMMARY

An embodiment of the present invention provides a blood flow rate measurement system. The system includes a catheter, a turbine, a signal generator and a signal lead. The catheter has a length. The catheter is configured to be inserted into a blood vessel of a living being, such as a human being. The turbine is disposed proximate a distal end of the catheter.

The turbine includes at least one blade. The at least one blade is configured to rotate. The at least one blade is configured to rotate relative to the catheter. The at least one blade is configured to rotate in response to fluid flow through the blood vessel. The at least one blade is configured to rotate at a rotational speed that depends at least in part on speed of the fluid flow through the blood vessel.

The signal generator is mechanically coupled to the turbine. The signal generator is configured to generate a signal indicative of the rotational speed of the at least one blade. The signal lead is configured to carry the signal indicative of the rotational speed of the at least one blade. The signal lead is connected to the signal generator. The signal lead extends along the catheter.

In any embodiment, the signal generator may include an electrical generator.

In any embodiment, the signal lead may include first and second electrically conductive leads and/or an optical fiber.

Any embodiment may include a tachometer. The tachometer may be coupled to the signal lead. The tachometer may be configured to measure the speed of the fluid flow through the blood vessel, based on the signal indicative of the rotational speed of the at least one blade.

In any embodiment, the at least one blade may be radially collapsible.

Any embodiment may also include a duct configured to direct at least a portion of the fluid flow through the blood vessel toward the at least one blade. The at least one blade may be configured to rotate, relative to the catheter, at a rotational speed dependent at least in part on shape and size of the duct.

In any embodiment, the duct may be radially collapsible.
In any embodiment, the duct may be tapered.

BRIEF DESCRIPTION OF THE DRAWINGS

The invention will be more fully understood by referring to the following Detailed Description of Specific Embodiments in conjunction with the Drawings, of which.

DETAILED DESCRIPTION

Embodiments of the present invention provide apparatus and methods for measuring blood flow, such as total blood flow due to natural heart action plus heart pump action, in a blood vessel of a patient when a catheter-based heart pump is inserted into the blood vessel, without relying on measurements of electric current drawn by a motor that drives the heart pump. Embodiments of the present invention include a turbine disposed at or near a distal end of the heart pump catheter. Rotation of the turbine blades is induced by blood or other fluid flowing through the blood vessel. The turbine is mechanically coupled to a signal generator, which generates a signal indicative of rotational speed of the turbine, which is dependent, at least in part, on speed of the fluid flowing through the blood vessel. The signal is carried by a lead to a proximal end of the catheter, external to the patient's body, where a tachometer calculates the blood flow rate from the rotational speed of the turbine. Advantageously, the lead is small in diameter.

Definitions

As used herein, the following terms shall have the following definitions, unless otherwise indicated:

A turbine is a rotary mechanical device that extracts energy from a fluid flow and converts the energy into useful work. The work produced by a turbine can be used for generating electrical power when combined with a generator. A turbine is a turbomachine with at least one moving part called a rotor assembly, which includes a shaft or drum with blades attached. Moving fluid acts on the blades so that they move and impart rotational energy to the rotor. (Wikipedia, turbine.) As used herein, turbines include, without limitation, Pelton, Francis and Kaplan turbines.

Reducing Diameter of Prior Art Heart Pumps

Figure 1:
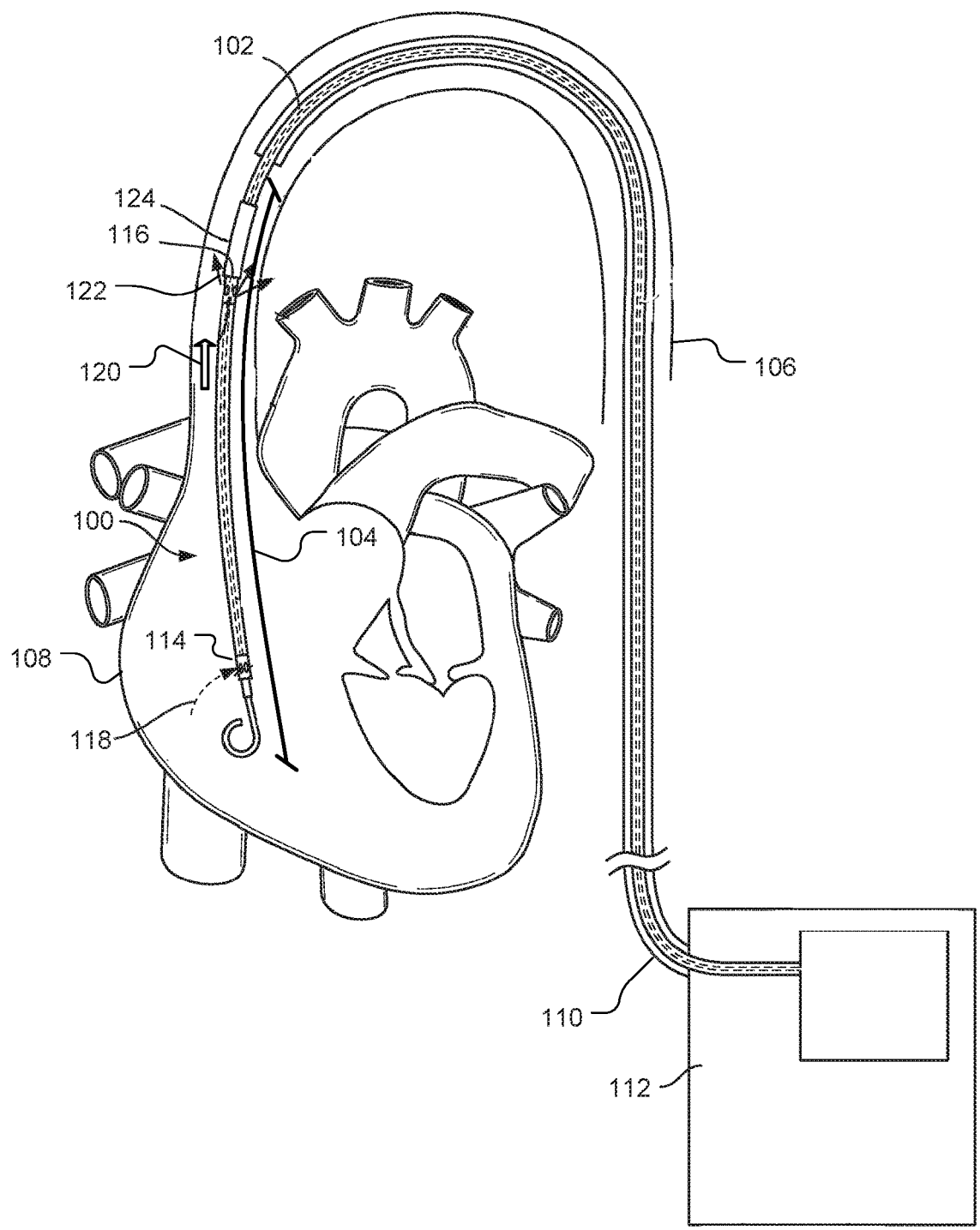
FIG. 1 illustrates a percutaneous left-heart pump inserted into a blood vessel of a patient, according to the prior art.

FIG. 1 shows an exemplary prior art heart pump 100 that includes an elongated catheter 102, a distal portion 104 of which is inserted through a blood vessel 106 into a heart 108 of a patient. A proximal end 110 of the catheter 102 is connected to an external control unit 112, such as an Automated Impella® Controller, available from Abiomed, Inc., Danvers, MA. Conventional heart pumps, such as the Impella 2.5® and Impella CP® heart pumps, include electric motors that drive impeller blades. Blood is drawn in through inlet ports 114 and expelled through outlet ports 116. Pumped blood flow is indicated by arrows 118, 120 and 122. Speed of a motor 124, and therefore speed of the pump 100 and amount of blood pumped, can be automatically ascertained by the control unit 112 by measuring electrical current drawn by the motor 124. However, as noted, the motor 124 is relatively large in diameter.

Relocating the motor 124 from the distal portion 104 of the catheter 102 to a location outside the patient's body, and driving the impeller blades with a flexible drive shaft (not shown) extending through the catheter 102, reduces the diameter of the heart pump 100. However, such a long, flexible drive shaft is subject to significant friction and other losses along its length. Therefore, the current drawn by an external motor is not a reliable indicator of the rotational speed of the impeller blades or of the amount of blood pumped by the heart pump.

Turbine-Based Blood Flow Rate Measurement System

Figure 2:
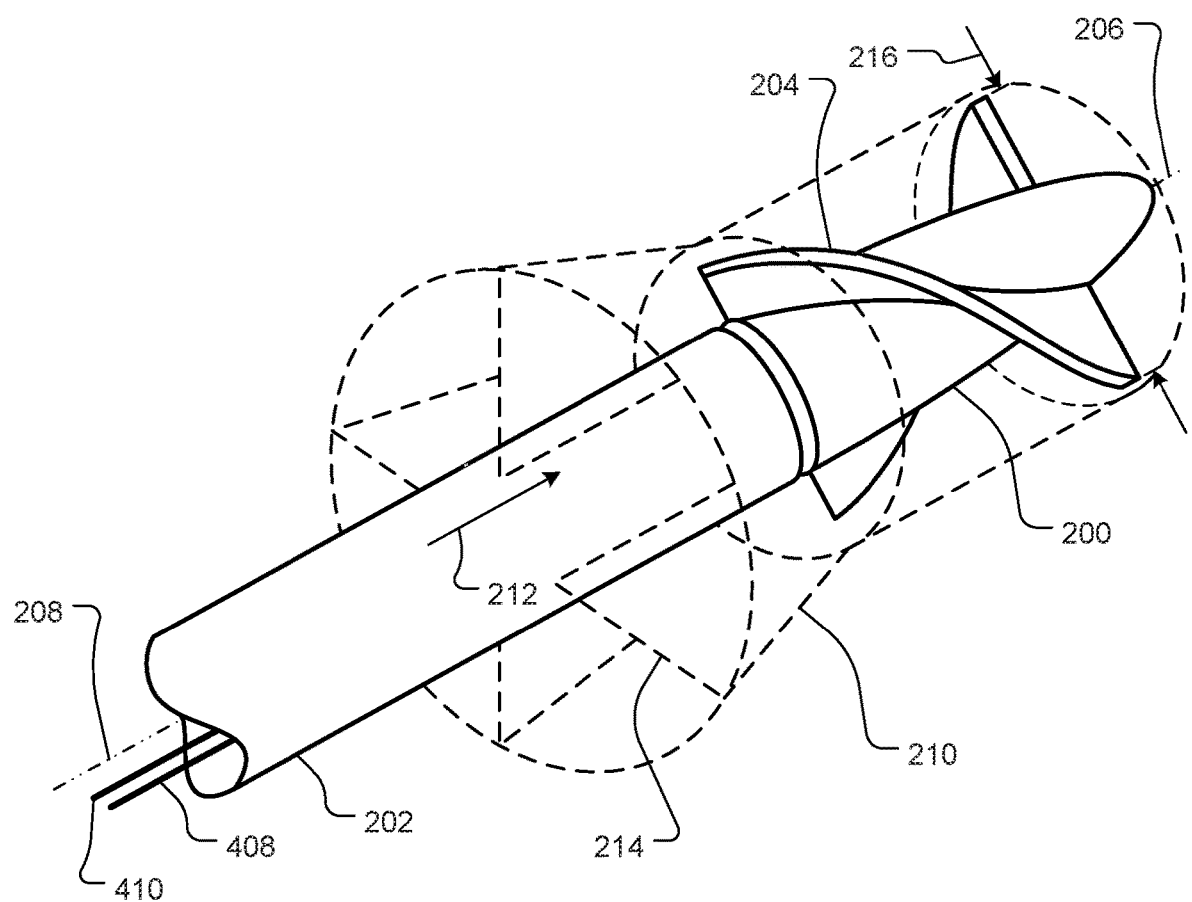
FIG. 2 is an isometric illustration of a distal end of a heart pump catheter with a turbine, and an optional duct, located at the end of the catheter to measure blood flow rate, according to an embodiment of the present invention.
Figure 3:
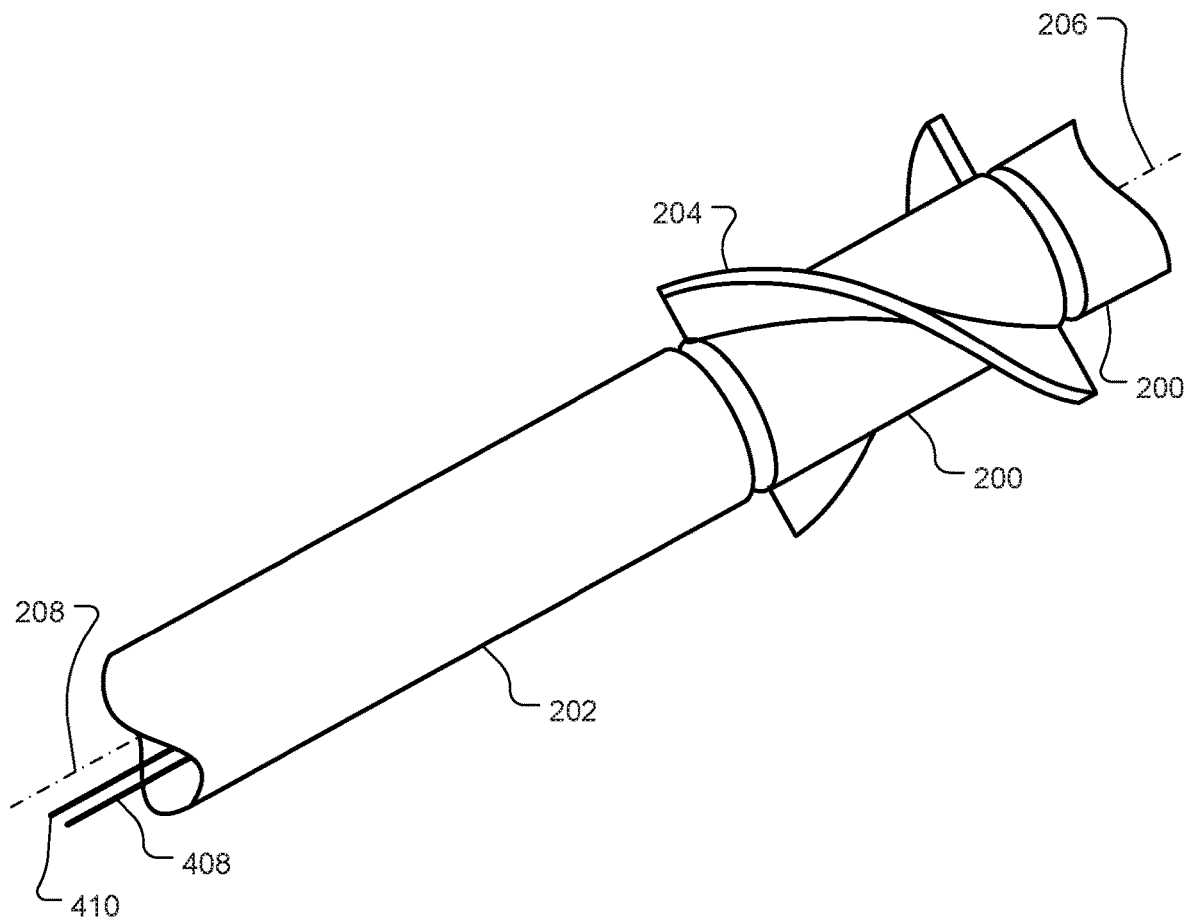
FIG. 3 is an isometric illustration of a distal end of a heart pump catheter with a turbine located near the end of the catheter to measure blood flow rate, according to another embodiment of the present invention.

To overcome this problem, and to provide reliable measurements of flow rate of a fluid through a blood vessel, an embodiment of the present invention includes a turbine 200 at or near the distal end of a catheter 202 that also includes a heart pump (not shown), as illustrated in FIGS. 2 and 3.

One or more blades 204 of the turbine 200 are driven to rotate, about an axis 206, by fluid, such as blood, flowing past the turbine 200 and impinging on the blades 204. The axis 206 may, but need not necessarily, align with a longitudinal axis 208 of the catheter 202. Optionally, a duct 210 (shown in phantom) may be included to protect the walls of the blood vessel during insertion and removal of the turbine 200, and to prevent the blades 204 engaging the walls, thereby preventing rotation of the blades 204, once the turbine 200 is in position. Optionally, the duct 210 may be tapered to increase rate of fluid flow 212 through the turbine 200. The duct 210 may, for example, be attached to the catheter 200 by rigid or collapsible fins, represented by fin 214. The optional duct 210 is omitted from FIG. 3 for clarity.

Figure 4:
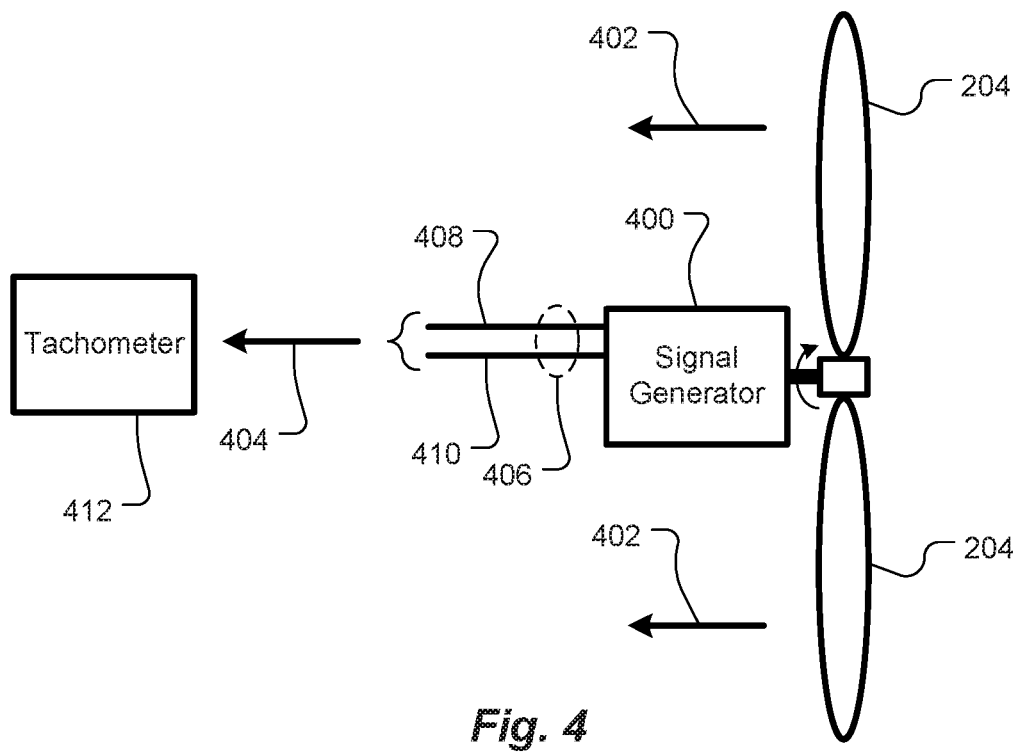
FIG. 4 is a schematic diagram of a signal generator mechanically coupled to the turbine of FIG. 2 or 3, according to an embodiment of the present invention.

The turbine 200 drives a signal generator 400, as shown schematically in FIG. 4. The signal generator 400 generates a signal 404 that is indicative of rotational speed of the turbine blades 204. The blades 204 are configured to rotate, relative to the catheter 202 (FIG. 2), at a rotational speed that is dependent, at least in part, on speed of the fluid 402 flowing through the blood vessel, and configuration of the duct 210 (if present), such as the taper of the duct 210.

The signal generator 400 is configured to generate the signal 404 indicative of the rotational speed of the blades 204. A signal lead 406, exemplified by two electric wires 408 and 410, is configured to carry the signal 404 to a tachometer 412. The tachometer 412 is configured to measure the speed of the fluid 402 flow (flow rate) through the blood vessel, based on the signal 404. In one embodiment, the tachometer 412 calculates the flow rate by multiplying the rotational speed of the blades 204 by a factor. The factor may represent a linear or non-linear relationship between rotational speed of the blades 204 and flow rate of the fluid 402. This relationship may be determined empirically or by modeling the blades 204, the fluid 402, blood vessel geometry, friction, etc.

Figure 5:
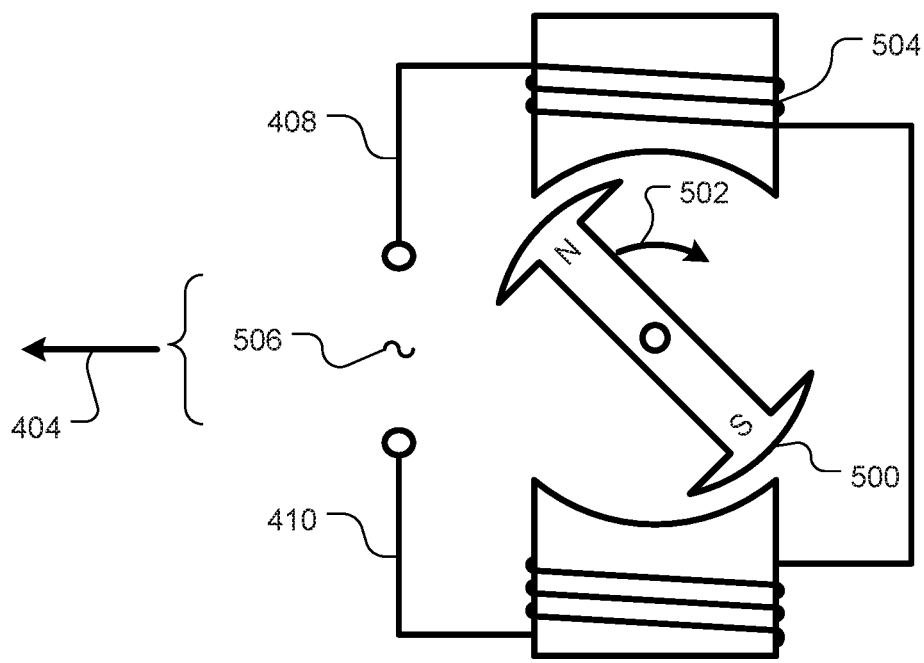
FIG. 5 is a detailed schematic diagram of the signal generator of FIG. 4, according to an embodiment of the present invention.

In one embodiment, schematically illustrated in FIG. 5, the signal 404 indicative of the rotational speed of the turbine blades 204 is an AC signal, in which frequency of the signal 404 is proportional to the rotational speed of the blades 204 (not shown in FIG. 5 for clarity). In one such embodiment, the blades 204 are mechanically coupled to a magnet 500, so the magnet 500 rotates with the blades 204, as indicated by an arrow 502. A coil 504 is disposed proximate the magnet 500. Each revolution of the magnet 500 induces a pulse (in this example, one cycle 506 of a sine wave) of the signal 404. The tachometer 412 may count the pulses (cycles) received during a predetermined time interval to measure the frequency of the signal 404. Although the coil 504 is shown with a core, any suitable core, such as an iron core or an air core, may be used. In addition, although the coil 504 is shown split into two portions, the coil need not be split.

Alternatively, the tachometer 404 may measure voltage of the signal 404, which is proportional to the rotational speed of the turbine blades 204.

Figure 6:
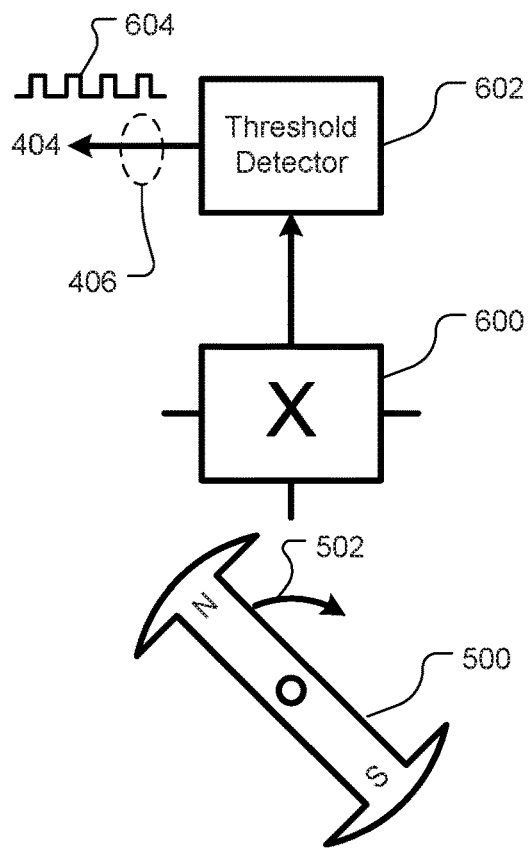
FIG. 6 is a detailed schematic diagram of the signal generator of FIG. 4, according to another embodiment of the present invention.

In another embodiment, schematically illustrated in FIG. 6, the coil 504 (FIG. 5) is replaced by a Hall effect sensor 600. An output signal from the Hall effect sensor 600 may be processed by a threshold detector 602 (if needed) to generate the signal 404 indicative of the rotational speed of the turbine blades 204 (not shown in FIG. 6 for clarity). In this embodiment, the signal 404 consists of rectangular pulses 604. As with the first embodiment described with respect to FIG. 5, the frequency of the pulses 604 is proportional to the rotational speed of the blades 204.

Figure 7:
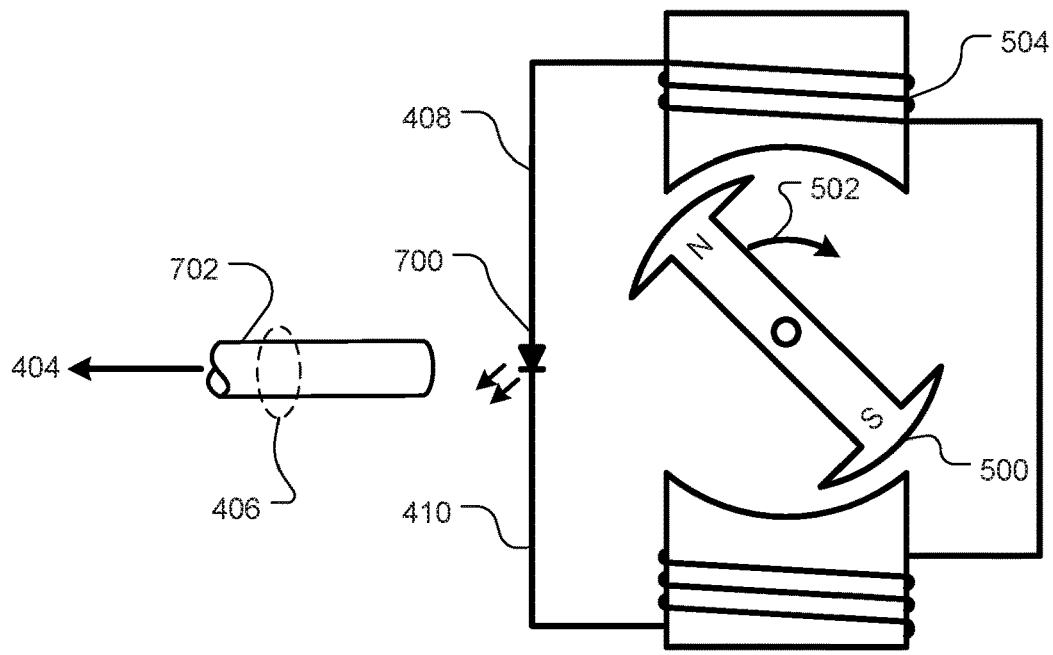
FIG. 7 is a detailed schematic diagram of the signal generator of FIG. 4, according to a third embodiment of the present invention.

In yet another embodiment, schematically illustrated in FIG. 7, the leads 408 and 410 from the coil 504 described with respect to FIG. 5 are connected to a light-emitting diode (LED) 700. The LED 700 is optically coupled to a distal end of an optical fiber 702. Each pulse (cycle) of the signal from the coil 504 causes the LED to flash, which sends an optical pulse along the optical fiber 702. A series of these optical pulses collectively form the signal 404 indicative of the rotational speed of the blades 204. Thus, in this embodiment, the optical fiber 702 is a lead 406 configured to carry the signal 404 to the tachometer 412, and the tachometer 412 includes an optical sensor (not shown) to detect the optical pulses.

In any embodiment, the lead 406 configured to carry the signal 404 may be discrete and extend along a lumen of the catheter 202. Alternatively, the lead 406 may be integral with the catheter 202. For example, in some embodiments, the wires 408 and 410 are printed on an outside and/or inside surface of the catheter 202, or imbedded within a wall of the catheter 202. Similarly, in one embodiment, the optical fiber 702 is imbedded within the wall of the catheter 202.

Although embodiments with one magnet per turbine have been described, each turbine can include more than one magnet, in which case the signal 404 may include more than one pulse per revolution of the blades 204.

Figure 8:
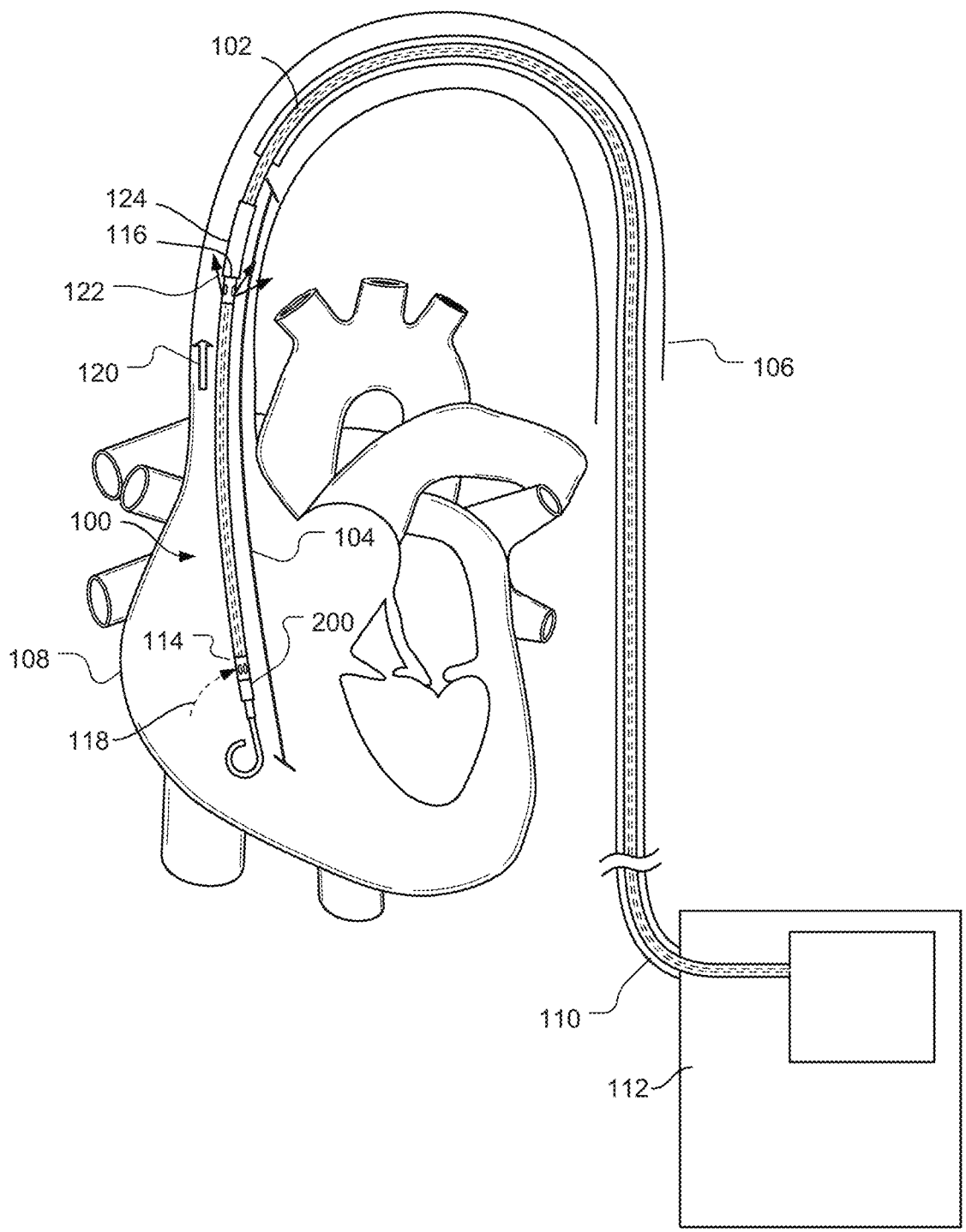
FIG. 8 illustrates a percutaneous left-heart pump inserted into a blood vessel of a patient, according to an embodiment of the present invention.
Figure 9:
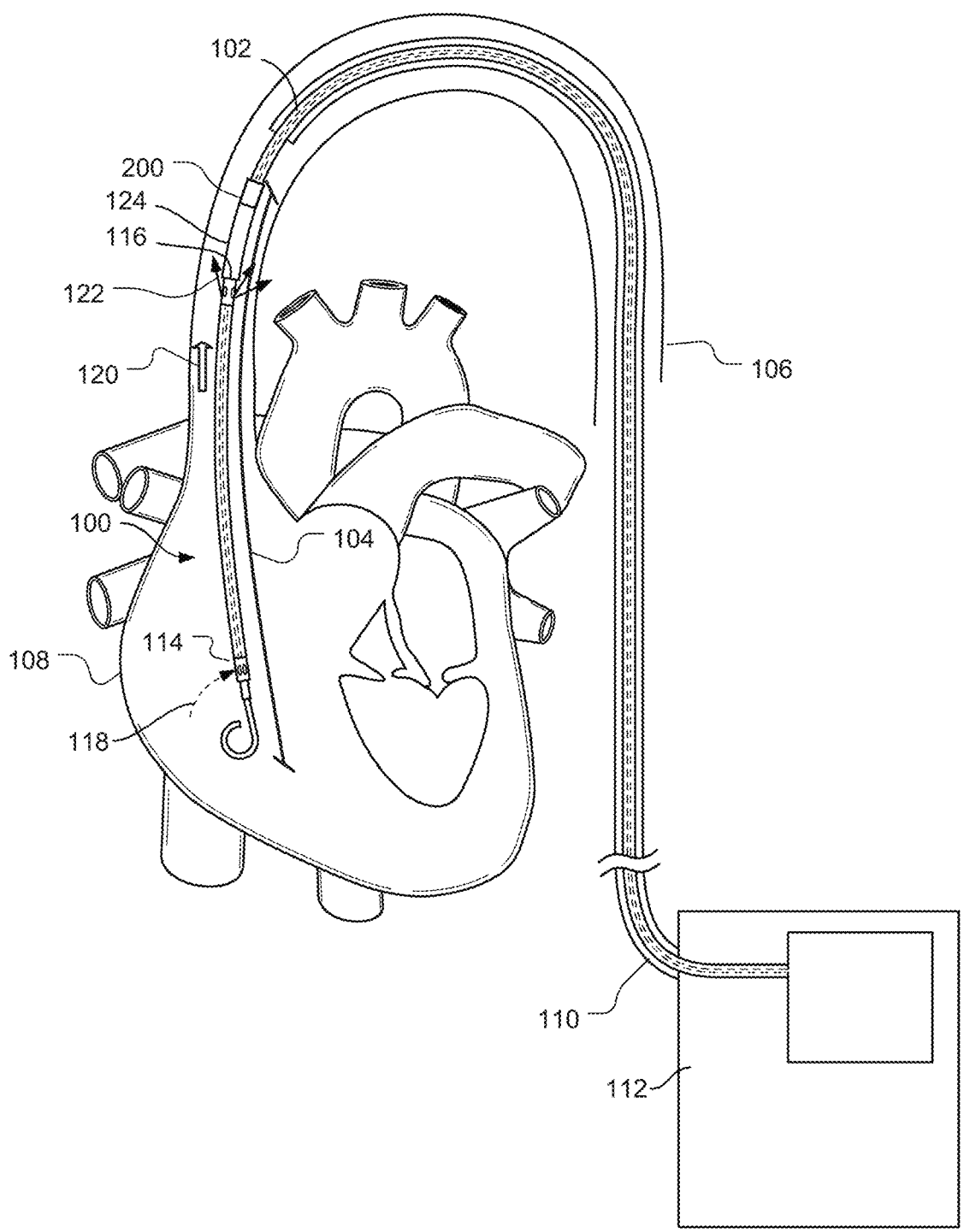
FIG. 9 illustrates a percutaneous left-heart pump inserted into a blood vessel of a patient, according to an embodiment of the present invention.
Figure 10:
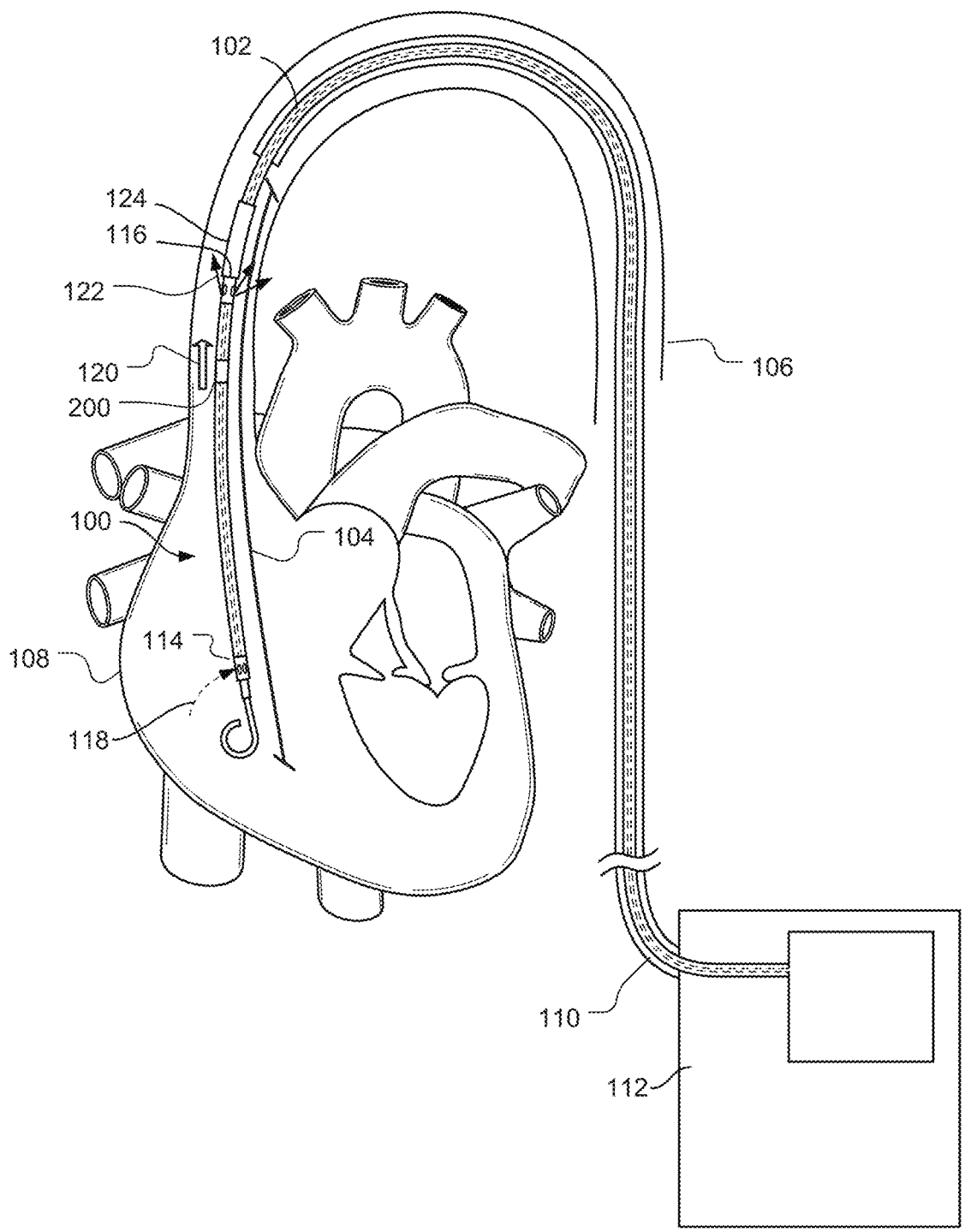
FIG. 10 illustrates a percutaneous left-heart pump inserted into a blood vessel of a patient, according to an embodiment of the present invention.

Although the heart pump pumps blood, the patient's heart action also pumps some blood. The total amount of blood flowing through the blood vessel is important to patient wellbeing. "Upstream" means in a direction opposite the direction of flow of blood or other fluid, and "downstream" means in the same direction as the flow of blood or other fluid. Advantageously, if the turbine is disposed a distance, in the upstream direction, from the heart pump inlet ports 114 (see, e.g., turbine 200 in FIG. 8) or a distance, in the downstream direction, from the heart pump outlet ports 116 (see, e.g., turbine 200 in FIG. 9), the blood flow rate measurement system embodiments described herein would measure total fluid flow in the blood vessel, not merely the amount of blood pumped by the heart pump. However, if the turbine is disposed between the heart pump inlet ports 114 and the heart pump outlet ports 116 (see, e.g., turbine 200 in FIG. 10), the blood flow rate measurement system would measure blood flow caused by heart action, plus additional blood flow around the heart pump caused by jet pumping driven by blood being ejected from the heart pump outlet ports 116.

Collapsible Turbine Blades

In some embodiments, the blades 204 are radially collapsible, i.e., in a direction toward the axis 206. In some such embodiments, the blades 204 are made of a flexible material that can be folded, shrunk or compacted to reduce outside diameter 216 (FIG. 2) of the blades 204, at least while the catheter is being inserted into a blood vessel. In some embodiments, the blades 204 are resilient. In some embodiments, the blades 204 are made of a shape-memory material that rebounds to its memorized shape upon being heated to a temperature equal to, or slightly less than, the temperature of circulating blood in a human body. In some embodiments, each blade 204 includes a plurality of struts that collapse or expand, depending on the mode (collapsed or expanded) of the blade 204. Consequently, once the catheter is in position, the blades 204 unfold or otherwise rebound into an efficient shape for being driven by flowing fluid in the blood vessel.

Any suitable structure and/or method may be used to initially make the blades 204 compact, to expand the blades 204 once the turbine 200 is in place, and to collapse the blades 204 in preparation for removal of the turbine 200. Exemplary structures and methods are described in U.S. Pat. Nos. 9,611,743, 9,416,783, 8,944,748, 9,416,791, 9,314,558, 9,339,596, 9,067,006, 9,642,984, 8,932,141, 8,814,933, 8,814,933 and 9,750,860, and U.S. Pat. Publ. Nos. 2018/0080326, 2014/0039465 and 2018/0296742, the entire contents of each of which are hereby incorporated by reference herein, for all purposes. Some of the structures and/or methods described in the aforementioned documents include wires or drive shafts to advance, retract and/or rotate components to expand or compress impeller blades and/or pumps. The same wires or drive shafts may be used in similar ways to actuate a structure configured to expand and/or compress the blades 204 of the turbine 200. Optionally or alternatively, different or additional wires or drive shafts may be used to actuate the structure configured to expand and/or compress the blades 204 of the turbine 200. Optionally or alternatively, the lead 406 or part of the lead 406 may be used to actuate the structure configured to expand and/or compress the blades 204 of the turbine 200.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The tachometer, heart pump control unit, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof. However, once programmed with these instructions, the combination of the processor and the memory collectively form a special purpose processor.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," for example as used to distinguish respective wires 408 and 410 from one another, are not intended to indicate any particular order or total number of items in any particular embodiment. Thus, for example, a given embodiment may include only a second wire and a third wire.

What is claimed is:

1. A system comprising:
   a catheter configured to be inserted into a blood vessel of a living being;
   a heart pump proximate a distal end of the catheter, wherein the heart pump is configured to be positioned across an aortic valve of the living being, and wherein the heart pump comprises at least one impeller blade, one or more inlet ports, and one or more outlet ports;
   a motor configured to be positioned at a location outside the living being and drive the at least one impeller blade, wherein rotation of the at least one impeller blade draws blood from a left ventricle of the living being into the one or more inlet ports and expels blood into an ascending aorta of the living being through the one or more outlet ports;
   a turbine proximate the distal end of the catheter and comprising at least one turbine blade, wherein the at least one turbine blade is configured to rotate, relative to the catheter, in response to fluid flow through the blood vessel and at a rotational speed dependent at least in part on speed of the fluid flow through the blood vessel, and wherein the turbine is disposed a distance, in an upstream direction, from the one or more inlet ports;
   a signal generator mechanically coupled to the turbine and configured to generate a signal indicative of the rotational speed of the at least one turbine blade; and
   a signal lead configured to carry the signal indicative of the rotational speed of the at least one turbine blade, wherein the signal lead is connected to the signal generator and extends through the catheter.

2. The system according to claim 1, wherein the signal generator comprises an electrical generator.

3. The system according to claim 1, wherein the signal generator comprises a magnet.

4. The system according to claim 3, further comprising a coil, wherein the magnet is configured to rotate, relative to the coil, in response to rotation of the at least one turbine blade.

5. The system according to claim 3, further comprising a Hall effect sensor, wherein the magnet is configured to rotate, relative to the Hall effect sensor, in response to rotation of the at least one turbine blade.

6. The system according to claim 1, wherein the signal lead comprises first and second electrically conductive leads.

7. The system according to claim 1, wherein the signal lead comprises an optical fiber.

8. The system according to claim 1, further comprising a tachometer coupled to the signal lead and configured to measure the speed of the fluid flow through the blood vessel, based on the signal indicative of the rotational speed of the at least one turbine blade.

9. The system according to claim 1, wherein the at least one turbine blade is radially collapsible.

10. The system according to claim 9, wherein the at least one turbine blade comprises a plurality of struts that collapse or expand.

11. The system according to claim 1, wherein the signal lead is configured to extend along the catheter to a location outside the living being.

12. The system according to claim 1, further comprising a duct configured to direct at least a portion of the fluid flow through the blood vessel toward the at least one turbine blade, wherein the at least one turbine blade is positioned inside the duct and configured to rotate, relative to the catheter, at a rotational speed dependent at least in part on a shape and a size of the duct.

13. The system according to claim 12, wherein the duct is radially collapsible.

14. The system according to claim 12, wherein the duct is tapered.

15. The system according to claim 12, wherein the duct is attached to the catheter by one or more fins.

16. The system according to claim 1, wherein the motor is configured to drive the at least one impeller blade with a flexible drive shaft extending through the catheter.

17. The system according to claim 1, wherein the at least one turbine blade is a helical turbine blade.

18. The system according to claim 1, wherein the turbine comprises two helical turbine blades, each of which is configured to rotate, relative to the catheter, in response to fluid flow through the blood vessel and at a rotational speed dependent at least in part on speed of the fluid flow through the blood vessel, and wherein the two helical turbine blades comprise the at least one turbine blade.

19. The system according to claim 18, wherein the two helical turbine blades extend helically around a hub of the turbine, and wherein a longitudinal axis of the hub aligns with a longitudinal axis of the catheter.

20. A system comprising:
    a catheter configured to be inserted into a blood vessel of a living being;
    a heart pump proximate a distal end of the catheter, wherein the heart pump is configured to be positioned across an aortic valve of the living being, and wherein the heart pump comprises at least one impeller blade, one or more inlet ports, and one or more outlet ports;
    a motor configured to be positioned at a location outside the living being and drive the at least one impeller blade, wherein rotation of the at least one impeller blade draws blood from a left ventricle of the living being into the one or more inlet ports and expels blood into an ascending aorta of the living being through the one or more outlet ports;

a turbine proximate the distal end of the catheter and comprising at least one turbine blade, wherein the at least one turbine blade is configured to rotate, relative to the catheter, in response to fluid flow through the blood vessel and at a rotational speed dependent at least in part on speed of the fluid flow through the blood vessel, and wherein the turbine is disposed between the one or more inlet ports and the one or more outlet ports;

a signal generator mechanically coupled to the turbine and configured to generate a signal indicative of the rotational speed of the at least one turbine blade; and a signal lead configured to carry the signal indicative of the rotational speed of the at least one turbine blade, wherein the signal lead is connected to the signal generator and extends through the catheter.

* * * * *